United States Patent
Y et al.

(10) Patent No.: US 10,311,401 B2
(45) Date of Patent: Jun. 4, 2019

(54) SYSTEM FOR CUSTOM CONFIGURING PERSONAL PROTECTION EQUIPMENT

(71) Applicant: Honeywell International Inc., Morris Plains, NJ (US)

(72) Inventors: Venkata Subbaiah Y, Bangalore (IN); Ashok Giri, Bangalore (IN); Kuldeep Sharma, Jhunjhunu (IN); Rachana K J, Mysore (IN); Sudeesh Thatha, Bangalore (IN); Neal Anthony Muggleton, Stevenage (GB); Sudhir Kamath, Houston, TX (US); Vishnu Vardhan, Bangalore (IN); Kushagra Thakur, Kankarbagh Patna (IN); Praveen Galagali, Bangalore (IN); Pierre Van Neste, Calgary (CA); Chinmaya Kar, Bangalore (IN); Liana Maria Kiff, Minneapolis, MN (US); Mohammed Ibrahim Mohideen, Bangalore (IN)

(73) Assignee: Honeywell International Inc., Morris Plains, NJ (US)

( * ) Notice: Subject to any disclaimer, the term of this patent is extended or adjusted under 35 U.S.C. 154(b) by 0 days.

(21) Appl. No.: 15/542,344

(22) PCT Filed: Jan. 5, 2016

(86) PCT No.: PCT/US2016/012122
§ 371 (c)(1),
(2) Date: Jul. 7, 2017

(87) PCT Pub. No.: WO2016/111970
PCT Pub. Date: Jul. 14, 2016

(65) Prior Publication Data
US 2018/0276598 A1     Sep. 27, 2018

(30) Foreign Application Priority Data
Jan. 9, 2015  (IN) ............................. 151/CHE/2015

(51) Int. Cl.
*G07F 17/00* (2006.01)
*G06Q 10/08* (2012.01)
(Continued)

(52) U.S. Cl.
CPC ........... *G06Q 10/087* (2013.01); *A41D 1/002* (2013.01); *A41D 13/00* (2013.01); *A41D 13/11* (2013.01);
(Continued)

(58) Field of Classification Search
None
See application file for complete search history.

(56) References Cited

U.S. PATENT DOCUMENTS 6,944,624 B2    9/2005 Orton et al.
2001/0011280 A1  8/2001 Gilbert et al.
(Continued)

FOREIGN PATENT DOCUMENTS

| WO | 2008144384 A1 | 11/2008 |
| WO | 2009020765 A1 | 2/2009 |
| WO | 2016111970 A1 | 7/2016 |

OTHER PUBLICATIONS

PCT Application No. PCT/US2016/012122, International Search Report, dated Mar. 9, 2016, 4 pages.
(Continued)

*Primary Examiner* — Timothy R Waggoner
(74) *Attorney, Agent, or Firm* — Craige Thompson; Thompson Patent Law

(57) ABSTRACT

Embodiments relate generally to a system having one or more computerized kiosks (102, 150, 160, 180, 192) oper-
(Continued)

able to associate a personal protection device (104) to a worker's personal information. In some embodiments, the kiosk (102, 150, 160, 180, 192) can use the worker's personal information to custom configure the personal protection device (104), so that the device (104) will better suit the needs of the specific worker.

20 Claims, 7 Drawing Sheets

(51) Int. Cl.
| | | |
|---|---|---|
| *G06Q 50/26* | (2012.01) | |
| *G07F 17/18* | (2006.01) | |
| *G06Q 20/18* | (2012.01) | |
| *A41D 1/00* | (2018.01) | |
| *A41D 13/00* | (2006.01) | |
| *A41D 13/11* | (2006.01) | |
| *G05B 15/02* | (2006.01) | |
| *A61F 11/14* | (2006.01) | |
| *B65G 43/00* | (2006.01) | |

(52) U.S. Cl.
CPC ............. *G05B 15/02* (2013.01); *G06Q 20/18* (2013.01); *G06Q 50/265* (2013.01); *G07F 17/0042* (2013.01); *G07F 17/18* (2013.01); *A41D 2600/20* (2013.01); *A61F 2011/145* (2013.01); *B65G 43/00* (2013.01)

(56) References Cited

U.S. PATENT DOCUMENTS

| | | | | |
|---|---|---|---|---|
| 2005/0244013 | A1* | 11/2005 | Battenberg | G01H 11/00 381/57 |
| 2009/0040014 | A1* | 2/2009 | Knopf | E04G 21/32 340/5.1 |
| 2010/0119074 | A1* | 5/2010 | Devinant | G01H 3/14 381/56 |
| 2010/0135502 | A1* | 6/2010 | Keady | A61B 5/121 381/58 |
| 2013/0094658 | A1* | 4/2013 | Holter | H04R 1/1083 381/72 |
| 2014/0278319 | A1* | 9/2014 | Thiruvengada | G06F 17/5009 703/11 |
| 2015/0091422 | A1* | 4/2015 | Adler | A61G 12/001 312/249.12 |

OTHER PUBLICATIONS

PCT Application No. PCT/US2016/012122, Written Opinion of the International Searching Authority, dated Mar. 9, 2016, 9 pages.

PCT Application No. PCT/US2016/012122, International Preliminary Report on Patentability, dated Jul. 11, 2017, 6 pages.

\* cited by examiner

SYSTEM FOR CUSTOM CONFIGURING PERSONAL PROTECTION EQUIPMENT

CROSS-REFERENCE TO RELATED APPLICATIONS

The present application claims priority to and is the National Stage of International Application No. PCT/US2016/012122 (entitled SYSTEM FOR CUSTOM CONFIGURING PERSONAL PROTECTION EQUIPMENT filed Jan. 5, 2016), which claims priority to India Provisional Patent Application No. 151/CHE/2015 (entitled SYSTEM FOR CUSTOM CONFIGURING PERSONAL PROTECTION EQUIPMENT filed Jan. 9, 2015), both of which are incorporated herein by reference.

STATEMENT REGARDING FEDERALLY SPONSORED RESEARCH OR DEVELOPMENT

Not applicable.

REFERENCE TO A MICROFICHE APPENDIX

Not applicable.

BACKGROUND

Currently, conventional personal protective equipment ("PPE") is typically used in a generic/uniform fashion, without taking into account any of the specific personal details related to the actual worker using the PPE. So, a generic type of PPE (out of any PPE category, such as respirators, face masks, protective suits, hearing protection devices, etc.) might be similarly assigned to all workers in an organization in a uniform fashion, without regard for their specific, individual needs. For example, conventional noise monitoring devices typically would use a generic noise exposure limit (for example, the maximum exposure allowed by law or regulation) in order to determine if a worker has been exposed to potentially damaging noise. Thus, current PPE devices do not take into account the fact that different workers may have different characteristics (such as previous hearing loss and/or previous exposure to potential dangerous levels of noise), which may result in different workers actually having different personal noise exposure limit levels (or other safety/protective needs). The disclosed embodiments may address these and similar problems, by for example, associating the PPE with relevant worker-specific personal information. And in some embodiments, the worker-specific personal information might even be used to custom configure the PPE, so that it better suits the individual worker's needs. In such ways, disclosed embodiments may improve personal protective equipment, helping to ensure that the PPE will actually function more effectively for a specific user/worker.

SUMMARY

In an embodiment, a computerized kiosk for configuring a personal protective equipment device is disclosed. The computerized kiosk comprises a processor, a non-transitory memory, and an application stored in the non-transitory memory. When executed by the processor, the application reads personal information about a worker who will use a personal protective equipment device (PPE) from a database and configures the PPE for use by the worker based on the personal information about the worker.

These and other features will be more clearly understood from the following detailed description taken in conjunction with the accompanying drawings and claims.

BRIEF DESCRIPTION OF THE DRAWINGS

For a more complete understanding of the present disclosure, reference is now made to the following brief description, taken in connection with the accompanying drawings and detailed description, wherein like reference numerals represent like parts.

FIG. 8A illustrates schematically (in a block diagram) a first exemplary kiosk embodiment, while

DETAILED DESCRIPTION

Figure 1A:
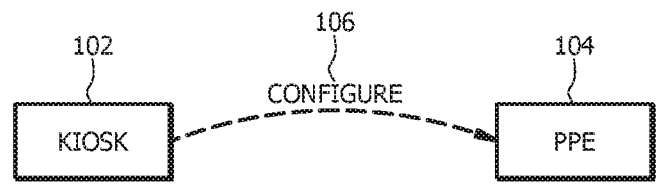
FIG. 1 illustrates schematically an exemplary system according to an embodiment of the disclosure having a computerized kiosk and a PPE, showing the two types of interactions between the computerized kiosk and the PPE in the exemplary system (although in some embodiments, the system might only perform one of these interactions), with FIG. 1A illustrating a kiosk operable to configure the PPE (for example, using or based on the personal information of the worker to whom the PPE is to be assigned/associated/provided), and FIG. 1B illustrating a PPE operable to upload PPE data or information to the kiosk.

It should be understood at the outset that although illustrative implementations of one or more embodiments are illustrated below, the disclosed systems and methods may be implemented using any number of techniques, whether currently known or not yet in existence. The disclosure should in no way be limited to the illustrative implementations, drawings, and techniques illustrated below, but may be modified within the scope of the appended claims along with their full scope of equivalents.

The following brief definition of terms shall apply throughout the application:

The term "comprising," "including," and/or "having" means including but not limited to, and should be interpreted in the manner it is typically used in the patent context;

The phrases "in one embodiment," "according to one embodiment," and the like generally mean that the particular feature, structure, or characteristic following the phrase may be included in at least one embodiment of the present invention, and may be included in more than one embodiment of the present invention (importantly, such phrases do not necessarily refer to the same embodiment);

If the specification describes something as "exemplary" or an "example," it should be understood that refers to a non-exclusive example;

The terms "about" or "approximately" or the like, when used with a number, may mean that specific number, or alternatively, a range in proximity to the specific number, as understood by persons of skill in the art field (for example, +/−10%); and If the specification states a component or feature "may," "can," "could," "should," "would," "preferably," "possibly," "typically," "optionally," "for example," "often," or "might" (or other such language) be included or have a characteristic, that particular component or feature is not required to be included or to have the characteristic. Such component or feature may be optionally included in some embodiments, or it may be excluded.

Generally, disclosed embodiments would relate to a system (and/or method) having one or more computerized kiosks (typically located in proximity to a work zone for a worker) operable to associate a personal protection equipment device to a worker's personal information (for example, by accessing a database or other memory/storage with personal information and/or communicating with the personal protection equipment device). While in some embodiments, such a database might be included as part of the kiosk, in other embodiments, the database might be remote data storage that is coupled to the kiosk (and/or to a terminal server). And in some embodiments, such a kiosk might use the worker's personal information (e.g. the personal information associated previously with the personal protective device) to custom configure the personal protection equipment device, so that the device may better suit the needs of the specific worker. Related method embodiments typically might associate a worker's personal information to a personal protective equipment device, and in some embodiments the associated personal information might then be used to custom configure the personal protective equipment in some way.

So, disclosed embodiments typically would be systems comprising a computerized kiosk and a personal protective equipment ("PPE") device (in other words, the kiosk would be operable for use with a PPE device, which might not necessarily be included as part of the system in some embodiments). Typically, the kiosk would be configured so that it is operable to associate the PPE with corresponding personal information (for example, relating to the worker to whom the PPE is being assigned). So for example, the worker might provide the kiosk (typically located in proximity to a work zone) with some form of worker identification (e.g. a worker unique identifier, for example, a PIN number (personal identification number) linked to that worker and operable to effectively identify the worker within the kiosk/database), along with some form of identification for the PPE which is being assigned the worker (e.g. a PPE unique identifier, for example, a serial number of the PPE being checked-out). While in some embodiments the worker identification and PPE identification might be entered into the kiosk by the worker (for example, using keypad, touchscreen, voice recognition commands, etc.), in other embodiments one or both of these identifications might be performed automatically by the kiosk (for example, using a camera with facial recognition, a proximity sensor operable to automatically detect PPE identification information, or communication between the PPE in the kiosk (for example, using wireless coupling (e.g. short range Bluetooth and/or long range 4G) and/or in conjunction with activation of PPE information transfer by the worker (for example, pressing a button on the PPE), etc. so that information transfer may occur either automatically or based on the PPE receiving a trigger (such as input activation from the worker pressing a button on the PPE, etc.)). In some embodiments, more than one form of identification might occur (for example, simultaneously), in order to double check the identity of the worker and/or the identity of the specific PPE being assigned to that worker. Thus, the kiosk may access and associate personal information from a database upon receiving one or more unique identifiers.

Typically, once identification information has been entered or otherwise transmitted/communicated or provided to the kiosk (typically in proximity to a work zone where the worker using the PPE will operate), the kiosk would then be able to associate (within its database/memory/storage) the particular PPE to the corresponding specific worker. This may allow tracking and/or monitoring, in order to know which PPEs have been assigned to which workers. Furthermore, the association (in the kiosk database, for example) between worker and PPE may allow worker-specific personal information to be linked with the PPE (for example, in the database). Such a link may be useful for allowing for analysis of information (for example, allowing supervisors to better manage distribution and/or maintenance of PPE devices).

In some embodiments, the PPE device itself may also collect/record information (for example, during the worker's shift in the work zone). Typically this type of recorded information from the PPE would relate to the functioning of the PPE itself (for example, recording any instances in which the PPE failed to effectively protect the worker from the hazard for which the PPE is being used), although in some embodiments the PPE could be configured and used to record any sort of data. Then, after the worker's shift, the PPE information/data might be uploaded to the kiosk (and thereby associated (e.g. included) with the worker's specific personal information, for example). Such association (in the kiosk database, for example) of PPE information with other worker-specific personal information may provide useful links for allowing analysis of the more detailed information (for example, allowing supervisors to better monitor compliance, safety incidents (for example, exposures over the limit, patterns, and schedules, etc.). Thus, in some such embodiments the PPE would be able to communicate with the kiosk. Such communication could be by wired or other physical electrical connection or wirelessly (for example, using Bluetooth, etc.). Furthermore, communication in some embodiments between the kiosk and the PPE might be two-way. In other words, the kiosk might be operable to communicate with the PPE, and the PPE might be operable to communicate with the kiosk. So at least at the time of association, the PPE and the kiosk may be communicatively coupled (e.g. the PPE and the kiosk may be operable to be communicatively coupled).

While collecting and correlating/associating PPE information with worker-specific personal information may be useful in allowing analysis to detect patterns, etc., in some embodiments the kiosk might also be operable to configure the PPE based on the corresponding personal information of the worker to whom the PPE is to be assigned. In this way, the kiosk may be operable to improve the functioning of the PPE device (which might now be termed a customized PPE device). As used herein, the term "configure" or the like can mean actively changing/altering the PPE device (e.g. the way the device technically operates), providing/associating/assigning only a proper/authorized PPE device to the worker, and/or refusing to provide/associate/assign a PPE device to the worker (for example, if the worker selects an inappropriate PPE in light of the worker's personal information) and offering guidance/recommendation to the worker regarding an alternate PPE which would be proper/authorized. When the kiosk configures the PPE device, it may improve the PPE to function better for the specific worker to whom the PPE is being assigned (for example, changing a generic/uniform PPE into a customized/personalized PPE device).

Examples of worker-specific personal information (depending for example, on the category of PPE at issue) might include a personal sound exposure limit (for example, based on hearing tests and or exposure history), personalized default volume setting, information on exposure history, information on job functions/tasks, information on authorized work zones, information on training requirements and/or records, information on medical history/flags, and/or other information relating to job history and/or job specifics. Of course, these are merely non-exclusive examples, and other personal information may also be associated with the PPE and/or used to configure the PPE. So, these sorts of personal information might be associated with the PPE (for example, at the time the PPE is assigned or checked-out to the worker). Depending on the PPE device, one or more of these sorts of personal information might also be used to configure the PPE to be worker-specific (e.g. specifically configured for the worker based on the worker's personal information). In this way, the worker's personal information can be used to custom configure the PPE.

Figure 1B:
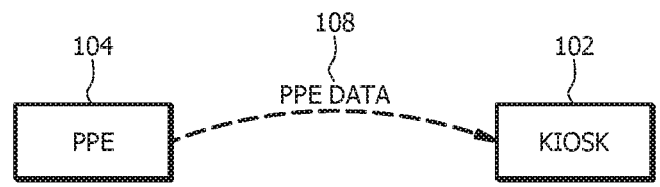

FIG. 1A and FIG. 1B illustrate an exemplary system having a computerized kiosk 102 operable to interact with one or more PPE devices 104. As shown in FIG. 1A, the kiosk 102 (typically located in proximity to a work zone) would be operable to configure 106 the PPE 104 in some manner, using the personal information of the worker to whom the PPE 104 is to be associated/assigned/provided. So for example, the worker could pick up an unassociated/unassigned PPE 104 and link it (for example, using a wired connection or other physical connection means such as a cradle, or a wireless means such as Bluetooth) to the kiosk 102 for association to the worker. By way of example, the worker might enter his PIN number, employee number, personal name, or other employee identification means/information (which the kiosk 102 might use to associate the PPE device 104 with the worker's personal information file, for example, in a database on the kiosk 102 or remotely located elsewhere), along with the serial number, RFID (radio frequency identity) number, or other identifier for the specific PPE device 104 at issue. The kiosk 102 might then use the worker PIN number to locate the appropriate file (for example, in a database) with the worker's personal information. The kiosk 102 might then use the personal information of the worker to configure the PPE device 104 in some manner (as shown in FIG. 1A, for example). Thus, the kiosk 102 may be configured to be a particular computer for communicating with the PPE 104 and/or worker, pulling specific personal information from a database, and/or using the specific personal information to configure the PPE 104. Additionally (or alternatively in some embodiments), after the worker's shift, the PPE 104 might be operable to upload PPE data 108 from the PPE 104 to the kiosk 102, for example, for association with (e.g. inclusion within) the worker's personal information (as shown in FIG. 1B). By way of example, some PPE devices 104 might be configured to store PPE data (for example, relating to operation of the PPE device 104 and/or exposure of the worker to some exposure level over a limit, especially when exposure relates to some hazard for which the PPE 104 is assigned to the worker to protect against). So, the worker would use the PPE 104 in a work zone during the work shift; and after the work shift, the PPE 104 might upload such recorded PPE data from the PPE 104 to the kiosk 102 (although in other embodiments, it may be possible that recorded PPE data might be uploaded in real-time, for example, using wireless communication). Thus in the embodiment of FIG. 1, the kiosk 102 would configure the PPE 104 based on the worker's personal information, and the kiosk 102 would also upload PPE data 108 from the PPE 104 (for example, to be included in the worker's personal information). In some embodiments, the worker might also disassociate the PPE 104 from the worker at the kiosk 102 (for example, returning the PPE 104 to the kiosk 102 after a work shift so that the PPE 104 might later be assigned/associated with another worker).

Figure 2:
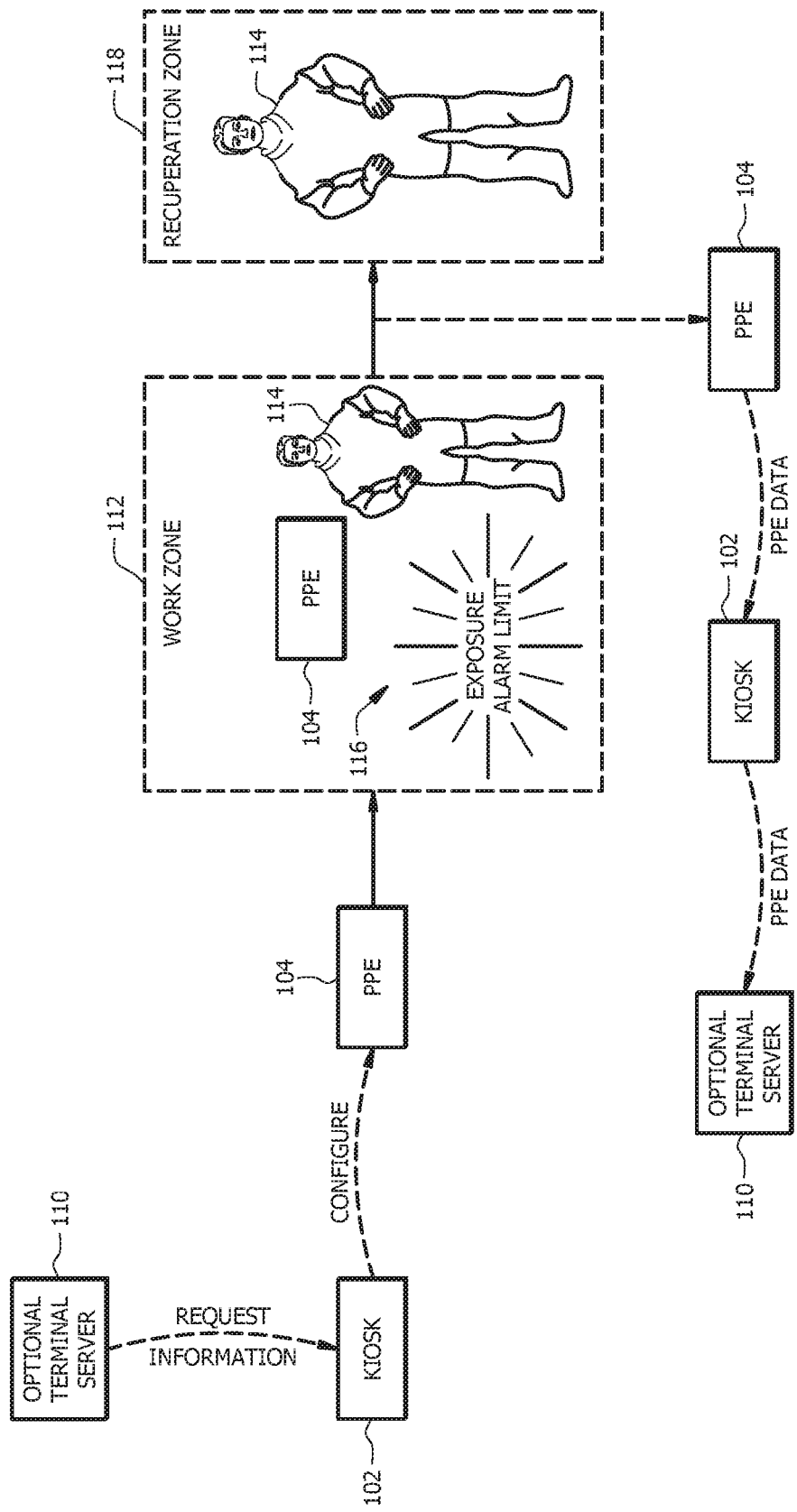
FIG. 2 illustrates schematically an exemplary system according to an embodiment of the disclosure having a computerized kiosk operable to configure the PPE, which is then used by the worker in a work zone; if there is an exposure in the work zone over the limit (as detected by the PPE for example), then the worker is signaled to leave the work zone and go to a recuperation zone; in some embodiments, the worker may (on his way to the recuperation zone, for example) download PPE data from the PPE to the kiosk; and in some embodiments, the kiosk may interact with an optional terminal server (for example, to download personal information about the specific worker and/or to upload PPE data)

FIG. 2 illustrates another exemplary system. In FIG. 2, the kiosk 102 (typically located in proximity to a work zone 112) uses personal information of the worker 114 to configure the PPE 104 (and as mentioned above, the term "configure" here means actively changing the PPE device 104 (e.g. the way the PPE device 104 technically operates, for example, re-programming the PPE device 104), providing/associating/assigning only a proper/authorized PPE device 104 to the worker 114, and/or refusing to provide/associate/assign a PPE device 104 to the worker 114 (for example, if the worker 114 selects an inappropriate PPE 104 in light of the worker's personal information) and/or offering guidance/recommendation to the worker 114 regarding an alternate PPE 104 which would be proper/authorized). In some embodiments, the kiosk 102 might download the personal information from an optional terminal server 110. Once the PPE 104 has been configured for the worker 114 to whom it is being assigned/associated, the worker 114 would typically take the PPE 104 into the work zone 112 in order to perform one or more work tasks. In the event that there is an exposure in the work zone 112 over the limit (for example, in the event that the PPE 104 is ineffective in protecting the worker 114 from the exposure in the work zone 112, such that (despite the PPE 104) the worker 114 is exposed to some hazard in excess of the safety limit), the PPE 104 might warn or signal the worker 114 to leave the work zone 112 (for example, using an audio and/or visual notification component 116). The worker 114 would typically then proceed to a safe zone or recuperation zone 118 for recuperation. For example, if the exposure is an excessively loud noise (for example, despite use of a hearing protective device PPE 104), then the worker 114 would typically go to a quiet zone; or if the exposure is to a particulate or chemical (despite a respirator PPE 104 or protective suit, for example), then the worker 114 might go to a zone with clean air. In some embodiments, the worker 114 might also (perhaps on the way to the recuperation zone 118) upload the PPE data to the kiosk 102 (which in some embodiments might then upload the information to an optional terminal server 110). FIG. 2 illustrates such an exemplary system. If there is no exposure over the limit, the worker 114 might still upload the PPE data to the kiosk 102 (and/or the terminal server 110), for association or inclusion with the worker's personal information. The optional use of a terminal server 110 (such as a cloud server) is discussed in greater detail below. Thus, a generic/uniform PPE 104 might couple with the kiosk 102 (and/or a terminal server 110), and then based on the worker unique identifier (and thereby the personal information associated with that worker unique identifier), the kiosk 102 might transform the PPE 104 from a generic, uniform PPE 104 into a customized/personalized PPE device 104.

In some embodiments, the kiosk 102 may have a plurality of bins (which may or may not be physically attached to the remainder of the computerized kiosk 102), each holding a different type of PPE 104 from within a category of PPE 104 for example (such a kiosk 102 might have multiple types of PPE 104 from a specific category of PPE 104). So for a PPE category of hearing protection devices, for example, the kiosk 102 might have a bin containing earplugs and a bin containing earmuffs (or alternatively two or more bins containing two different earplug and/or earmuff devices with different characteristics). The kiosk 102 might then be able to use the worker specific personal information to recommend which type (perhaps including a combination of types) of such available PPE 104 would be appropriate for the specific worker 114. For example, if the worker's personal information indicated that the worker 114 has already suffered hearing damage and/or recent exposure to potentially damaging noise, the kiosk 102 could recommend the most protective type of hearing protective device available (for example, in the bins); and in some embodiments, the kiosk 102 could recommend combining earplugs with earmuffs (to provide two-tiers of protection, if needed). In other more automated embodiments, the bins with multiple types of PPE in a PPE category (e.g. with each bin having a different one of the multiple types of PPE 104 in a PPE category) might be sealed (in a manner preventing workers from selecting their own PPE 104), and the kiosk 102 might automatically retrieve the appropriate PPE 104 based on the specific individual worker's personal information. So in such embodiments, the kiosk 102 might automatically provide the worker 114 with the appropriate PPE 104 based on the worker's personal information (and in this way, configure the PPE 104 based on the worker's personal information). So for such an exemplary system, the worker 114 might provide worker identification information, and the kiosk 102 might then retrieve the worker's personal information and use that personal information to select the appropriate PPE 104 from the plurality of bins (then perhaps, for example, automatically associating the PPE serial number (which might be scanned automatically) with the worker's personal information in the database).

An example might further clarify these concepts. In this example, the PPE 104 might be a hearing protection device ("hpd") and a noise exposure monitoring component, where the noise exposure monitoring component may be operable to record protected noise exposure (e.g. noise exposure under the hearing protection device) and may be operable to warn the worker 114 (for example, with a visual and/or audio signal) if protected noise exposure exceeds a preset limit. An example of such a PPE device 104 would be Honeywell's QuietPro™ device, in which the noise exposure monitoring component and the hpd are integrated into a single PPE device 104. Typically, such a noise exposure monitoring device would include a processor, memory/storage (for recording noise exposure data and/or for storing the generic limit and/or a personal limit—as programmed by the kiosk 102, for example), and a microphone (located under the hearing protection device) for detecting noise level for recording in the memory. In some embodiments, the processor would be configured (for example, as a particular computer) to compare the recorded/detected noise level to the limit, and to transmit or display an alarm/alert in the event that the protected noise exposure level exceeds the limit. In some embodiments, at least a portion of the storage/memory might be operable to be altered (for example, by the kiosk 102 setting the personal limit, with the processor then operable to read/use this limit—further configuring the PPE device 104 as a particular machine specifically for the needs of the worker 114) and at least a portion of the storage/memory might be operable to record detected noise exposure and/or to be read by the kiosk 102 (for example, for uploading of recorded noise exposure data). Typically, the PPE device 104 might also have some communication means (for example, a receiver and/or transmitter), allowing communication with the kiosk 102 (for example, for configuring the PPE device 104 with the personal noise exposure limit and/or uploading PPE data to the kiosk 102).

So, the kiosk 102 might configure such a PPE 104 by setting the personal sound exposure limit of the noise exposure monitoring component using the personal information of the worker 114. So for example, even if the standard generic noise exposure limit (for example, based on the law) is 85 dB, the kiosk 102 might configure the PPE 104 to have a lower personal sound exposure limit in instances where hearing tests indicate the worker 114 has already suffered hearing damage and/or prior exposure information indicates the worker 114 has previously been exposed to potentially damaging noise levels. In other words, when the kiosk 102 associates the PPE 104 with the worker 114, it would instruct/set the PPE 104 to use the worker's personal sound exposure limit (instead of a generic limit) as the threshold to trigger a warning/alert (thereby notifying the worker 114 to leave the work zone 112 and go to a quiet zone to recuperate, for example). In doing so, the kiosk 102 might override the generic/uniform limit (instead inserting the personal limit), or might delete a prior personal limit (for example, from another worker 114) and insert a new personal limit. Such changes typically might be to software, hardware, and/or firmware. In this way, the interaction between the kiosk 102 and the PPE 104 may improve functionality of the PPE 104 so that it may be better suited for the individual needs of the specific worker 114. Thus, the kiosk 102 might use the worker's specific personal information to configure the hpd with noise exposure monitoring ("HPNM", for example, a QuietPro™ PPE, actively changing the noise exposure limit based on the personal information of the worker 114 (resulting in a PPE device 104 that is a personalized/customized alert device, which has been custom configured to the specific worker 114). In other words, the kiosk 102 might configure the HPNM hpd PPE by overriding the standard exposure limit for the device, so that alerts might instead be triggered based on the worker's personal sound exposure limit personal information. In some embodiments, the HPNM device might originally have a generic noise exposure limit as its pre-set, which would be overridden or bypassed by the kiosk 102 (to instead set the HPNM device to use the worker's personal noise exposure limit). In such instances, after the worker 114 is done using the device (e.g. the device is disassociated from the worker), it may reset automatically to the generic limit in some embodiments (unless or until it is re-associated or reprogrammed by the kiosk 102 for the next worker). In other embodiments, the kiosk 102 may erase any previously set personal limit (for example, from another worker 114 to whom the device was previously assigned), and then download the new personal limit based on the current worker's personal noise exposure limit (from the personal information). In this way, the kiosk 102 may alter the device to configure it for the current worker 114, based on that worker's personal information. And while the worker's personal exposure limit would typically be based on audiogram testing or other medical records, the limit might also in some instances be set to take into account the location and/or job task and/or organization level compliance information as well.

Some such hearing protection devices, such as QuietPro™ for example, might also include listen through capabilities and/or radio/communication capabilities. For example, the PPE 104 might include a sound pass-through component (such as an external microphone outside the hearing protection device and a speaker located under the protection device) operable to transmit external sound through to the user and/or a wireless communication component (with the receiver linked to a speaker under the hearing protection device) operable to transmit communication broadcasts into the worker's ear under the hearing protection device. For such PPE devices 104, the kiosk 102 might further configure the PPE 104 using personal information of the worker 114, for example, to set the default volume level for the PPE 104 (for example, for either the sound pass-through or wireless communication). And in some embodiments, the kiosk 102 might configure the PPE 104 for the preferred language listed in personal information of the worker 114 (so for example, the PPE 104 might provide warnings, instructions, and/or feedback in the correct language). The kiosk 102 may be operable to further configure the PPE 104 in other embodiments, for example, setting the maximum adjustable volume level based on the personal information of the worker 114 and/or checking to see if the worker 114 has recently been exposed to noise over the limit (such that the worker 114 might need additional recuperation time before being exposed to noise environment again), and if so refusing to associate/provide/assign a PPE 104 to the worker 114 until sufficient time is passed for recuperation. And as mentioned above, the kiosk 102 might also (or alternatively) have multiple types of hearing protection PPE 104 available, and the kiosk 102 might recommend or provide the appropriate hearing protection PPE 104 based on the worker's personal information. For example, the kiosk 102 might recommend earmuffs rather than earplugs (or by way of example, QuietPro™), or might recommend the use of earmuffs over earplugs (e.g. in combination) based on the worker's personal information. This may be another way in which the kiosk 102 could configure the hearing protection PPE 104, for example. The hearing protection examples discussed above are merely illustrative, and the system (for using the kiosk 102 to associate the PPE 104 with the worker's personal information and/or to configure the PPE 104 based on the personal information) could be used for various categories of PPE 104.

As mentioned above, in some embodiments the kiosk 102 may upload recorded/measured PPE data/information from the PPE 104 (for example, after worker's shift), see FIG. 1B for example. In some embodiments, the kiosk 102 (typically located in proximity to a work zone 112 for a worker's shift) might also be operable to communicate with a terminal server 110 (typically located remotely from the work zone 112 and/or kiosk 102) (e.g. the kiosk 102 and the terminal server 110 might be communicatively coupled). In such an arrangement, the terminal server 110 would typically store (remotely in a database, for example) the personal information of the worker 114 (for example, having database files for each worker 114 who would (by job function, for example) be likely to interact with the kiosk 102). In other words, the terminal server 110 typically might be operable to communicate with one or more kiosks 102, to simultaneously configure and/or manage multiple PPE devices 104 for a plurality of different workers 114 (and/or to simultaneously upload and associate PPE data from a plurality of PPE 104 with a plurality of worker personal information files in a database). So, the terminal server 110 may be configured as a particular computer able to access (e.g. read/write to) a database with personal information files organized for specific workers 114 and to communicate with the kiosk 102, while perhaps also allowing searches and/or automated pattern detection within specific worker files and/or across a plurality of worker files (for example, organizationally and/or across departments). Thus, the kiosk 102 would be able to pull the worker-specific personal information from the terminal server 110 (for example, using the worker PIN number to identify the correct file), and then might use that personal information to configure the PPE 104. So typically, the kiosk 102, terminal server 110, and/or PPE 104 might all need to be configured to intermesh/interact effectively (e.g. in a particular manner), in order to provide a cohesive, unified system. In some embodiments, the terminal server 110 might be a cloud server.

Figure 3A:
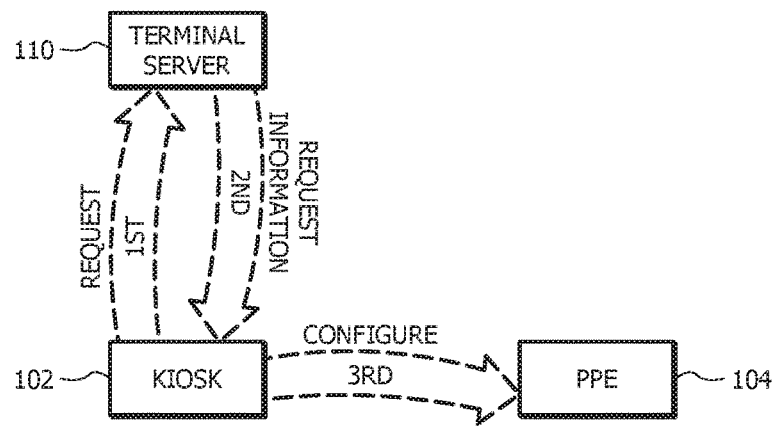
FIG. 3 illustrates schematically an exemplary system according to an embodiment of the disclosure in which the kiosk is operable to interact with both the PPE and a terminal server (showing two different interactions in such a system, although in some embodiments the system might perform only one of these interactions); for example, in FIG. 3A, the kiosk might download from the terminal server personal information about the worker to whom the PPE is being assigned/associated, and might use that personal information to configure the PPE, while in FIG. 3B the kiosk might upload the PPE data from the PPE and then transmit/upload the PPE data to the terminal server.
Figure 3B:
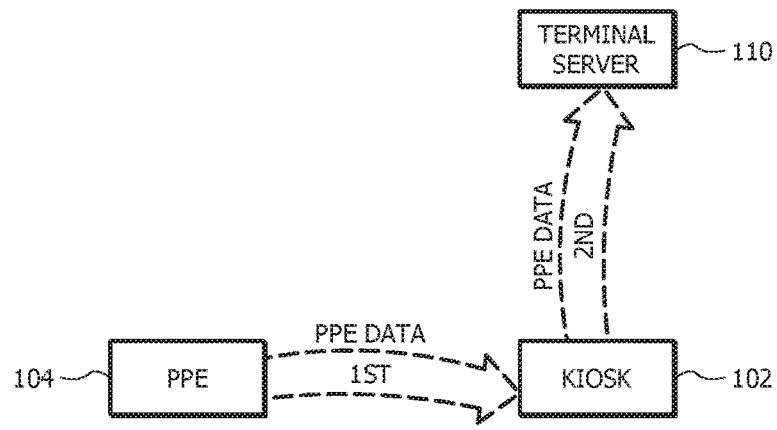

FIG. 3 illustrates such an exemplary system, having a terminal server 110, a computerized kiosk 102, and a PPE device 104. In FIG. 3A, the worker 114 might attempt to associate the PPE device 104 with the worker 114 (e.g. check-out the PPE device 104). Upon activation (e.g. for association), the kiosk 102 would typically request the worker's personal information from the terminal server 110, and in response, the terminal server 110 would typically download the requested worker-specific personal information to the kiosk 102. In other words, the kiosk 102 and the terminal server 110 would be configured to communicate with each other, so that the kiosk 102 might send the worker identification information to the terminal server 110 (to allow for identification of the proper file related to the correct worker 114), and then the kiosk 102 might receive from the terminal server 110 the requested personal information. In some embodiments, the kiosk 102 might also send the PPE identification information (e.g. serial number) to the terminal server 110 to be associated in the database with the worker's personal information (for example, so it is clear which PPE device 104 has been assigned to the worker 114, and so that related PPE data may later be uploaded and associated/included with the personal information). The kiosk 102 might then configure the PPE 104 using the worker's personal information (as discussed above, for example). In embodiments in which the PPE 104 records PPE data (during the work shift for example), after the work shift (or optionally at some other time, even in real-time in some embodiments), the PPE 104 might upload PPE data to the kiosk 102, which might then in turn send that data to the terminal server 110 (where it might typically be associated with or added to the worker-specific personal information—thereby altering or amending the personal information file stored on the terminal server 110 to some degree, for example), as shown in FIG. 3B. Of course, in some embodiments, PPE data might be uploaded during the work shift (for example, in real-time if the PPE 104 and the kiosk 102 are linked by a communication means that operates over a greater distance) or at some other time.

Figure 4:
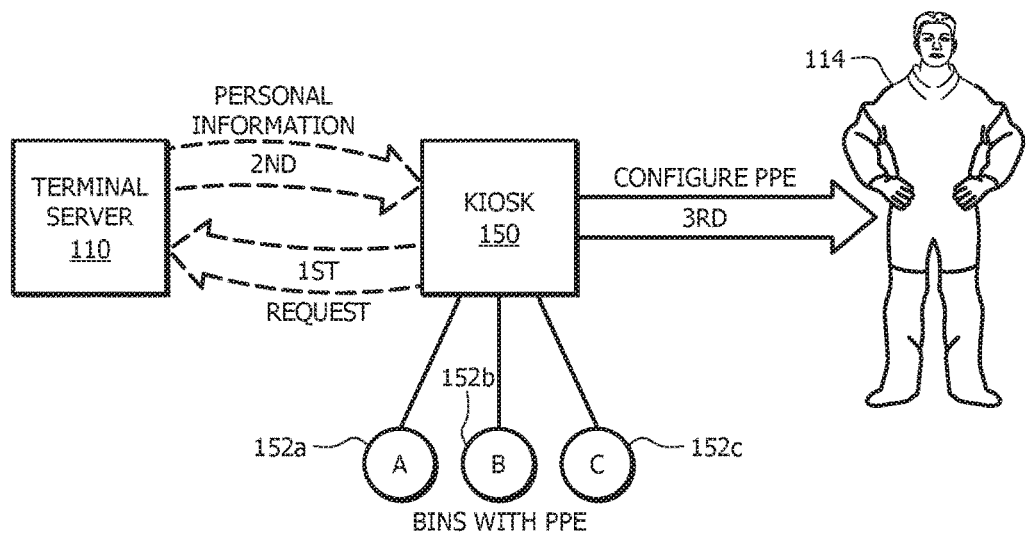
FIG. 4 illustrates schematically an exemplary system according to an embodiment of the disclosure having a kiosk with a plurality of bins (with each bin having a different type of PPE from the same PPE category, for example), wherein the kiosk downloads personal information about the worker from the terminal server and automatically provides/associates/assigns the correctly configured PPE from the bins to the worker based on the personal information.

And as mentioned above, the kiosk 102 could in some embodiments include multiple bins (which might for example, be physical receptacles for holding a plurality of PPE devices 104, such as baskets, hampers, canisters, lockers, etc.) having PPE devices 104 (with each bin having one of a plurality of PPE types from a PPE category for example). Thus, the kiosk 102 could provide various PPE options, which might be recommended or provided to the worker 114 based on the worker's personal information. In other words, the kiosk 102 might configure the PPE device 104 for the worker 114 using the options available from the plurality of bins to best fit the worker 114 based on the worker's personal information. FIG. 4 illustrates such an exemplary system. So in FIG. 4, when worker 114 requests a kiosk 150 to associate a PPE device 104, the kiosk 150 might request the worker-specific personal information from the terminal server 110 (via a communication link, which could be wired or wireless or might include a cloud network). The terminal server 110 would then transmit the requested personal information to the kiosk 150. The kiosk 150 might then use the personal information, along with the available PPE options in the bins 152, to configure the PPE 104 for the worker 114 (to try to better suit the worker's needs). So for example, if the bins 152 are open bins from which the worker 114 might select PPE devices 104, the kiosk 150 might recommend a PPE device 104 and/or reject an inappropriate PPE device 104. Alternatively, if the bins 152 are closed/sealed/locked (so as to be unavailable to the worker 114 directly, but rather require the kiosk 150 to automatically dispense the PPE 104 from the bins 152), then the kiosk 150 might automatically select the appropriate PPE 104 and automatically provide/dispense it to the worker 114 (thereby associating/assigning that PPE device 104 with the worker 114—such PPE association might also be transmitted to the terminal server 110, for example, for association with (e.g. inclusion within) the personal information). Thus, some embodiments may utilize an automated and/or mechanized delivery system as part of the kiosk 150. For example, the kiosk 150 might, in response to the worker unique identifier, access the personal information to determine the appropriate PPE 104 from the available selections in the bins 152, and then might actuate a physical mechanism to release the customized PPE 104 (for example, unlocking a bin 152 or actuating an arm to retrieve PPE 104 from the bins 152, or actuating a transport device to physically move the PPE 104 from the closed bin to an opening (e.g. a slot) for retrieval). So, in FIG. 4, the kiosk 150 may use the personal information of the worker 114 (obtained from the terminal server) to provide a configured PPE device 104 to the worker 114.

In some system embodiments, the system may comprise a plurality of kiosks 150 (often positioned in different locations), with each kiosk 150 operable to communicate (typically at a distance) with a terminal server 110 (similar to the system(s) described above). In such systems, all organizational personal information (which might include personal information of many or all workers 114 in an organization who might use such kiosks 150) would typically be stored at the terminal server 110 (for example, in a database), and the kiosk 150 would typically act as a relay for allowing communication between the terminal server 110 and the PPE 104. Thus, the kiosks 150 might each be operable to communicate with the terminal server 110 to download personal information for use configuring the PPE 104 (as shown for example, in FIG. 5A). And in some embodiments, the kiosk 150 might also be operable to upload data from the PPE 104 (e.g. noise exposure measurement data from QuietPro) to the terminal server 110, where the PPE data might be associated with the personal information of the worker 114—e.g. in the database (as shown in FIG. 5B). Such an association of data in the database might allow for analysis (for example, detecting patterns), which could improve worker safety and/or project management (such as organizational compliance, for example).

Figure 5A:
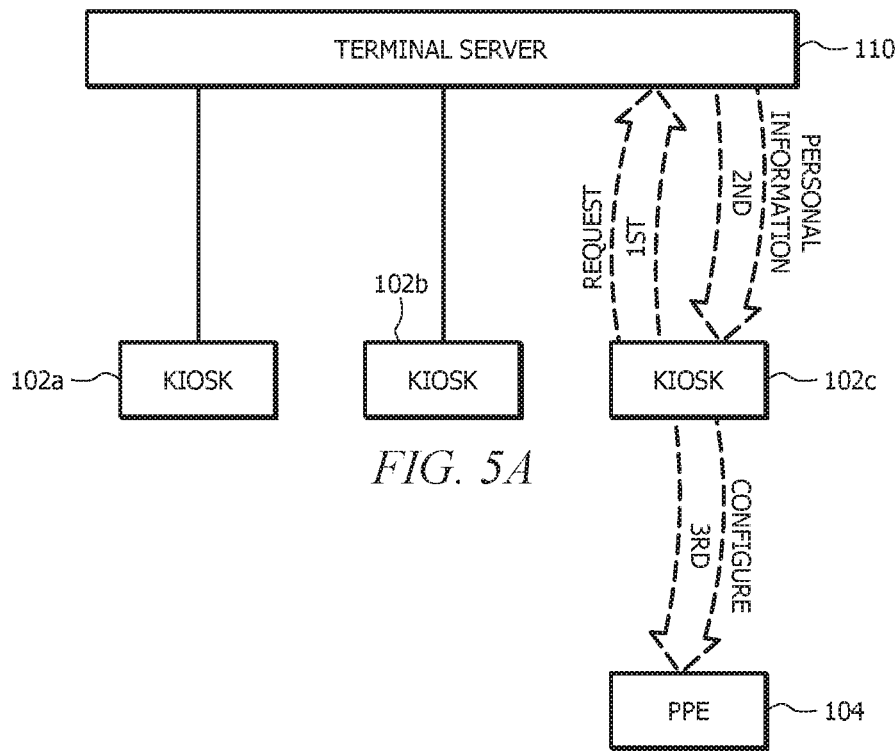
FIG. 5 illustrates schematically an exemplary system according to an embodiment of the disclosure in which a terminal server is operable to interact with a plurality of kiosks (showing two different interactions in such a system, although in some embodiments the system might perform only one of these interactions), with FIG. 5A showing one of the kiosks being used to download personal information from the terminal server and then configuring the PPE based on that personal information, and FIG. 5B showing the PPE uploading PPE data to one of the plurality of kiosks, which then transmits/uploads the PPE data to the terminal server.
Figure 5B:
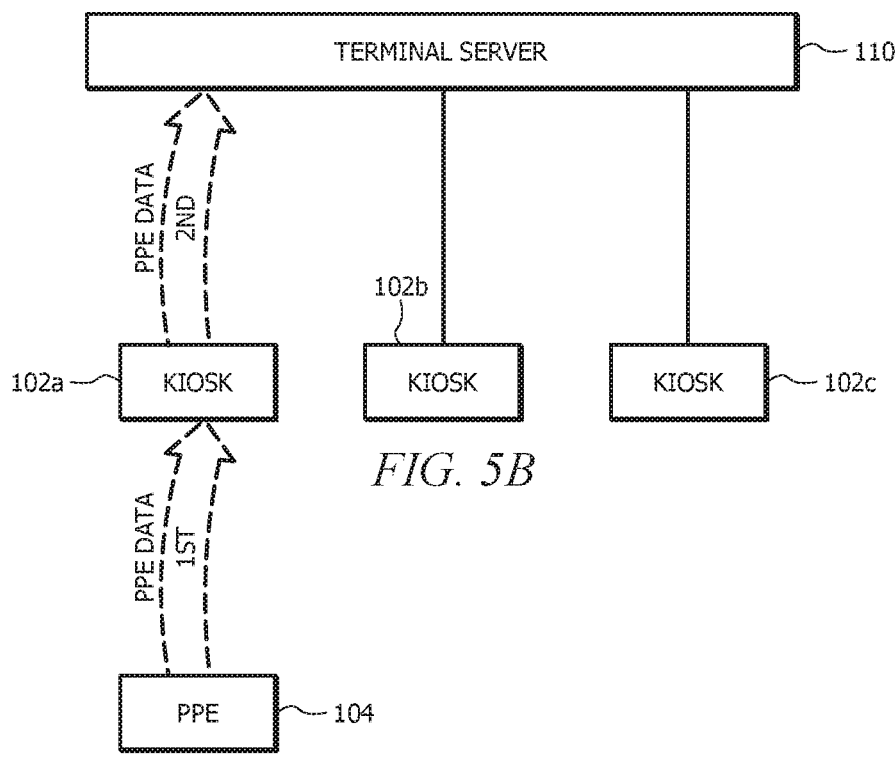

So for example, (as shown in FIG. 5A), a worker 114 might access one of the plurality of kiosks 102 (for example, a first kiosk 102*a*, a second kiosk 102*b*, and a third kiosk 102*c*) in attempt to check-out the PPE 104 and/or associate the PPE 104 with the worker's personal information. The kiosk 102 would typically send a query/request to the terminal server 110 (which might include the worker identification information), and in response the terminal server 110 might download the appropriate personal information (corresponding to the identified worker 114) to the kiosk 102, which might then transmit data to the PPE 104 or otherwise configure the PPE 104 (for example, allowing the kiosk 102 to configure the PPE 104 based on the personal information). In some embodiments, the kiosk 102 might also send PPE identification information to the terminal server 110, for association with the personal information in the database (as described above, for example). After the work shift, the worker 114 might use the kiosk 102 to upload PPE data (for example, noise exposure measurement data) from the PPE 104 to the terminal server 110, where the PPE data might be associated in the database with the specific worker 114 and/or that worker's personal information (as shown in FIG. 5B). Such an association in the database might also make use of the PPE identification information. And in some embodiments, the worker 114 might check-in the PPE device 104 back at the kiosk 102 as well, disassociating the worker 114 with the PPE device 104 (for example, so that the database no longer shows that the specific PPE device 104 has been assigned to that specific worker 114) and perhaps placing the PPE device 104 in a bin 152 so that it might later be re-assigned to a new or different worker 114.

By uploading PPE data (such as noise exposure measurements) to the terminal server 110 (or other database), such data can be analyzed and issues might be identified and/or reported (for example, to supervisors). In some embodiments, uploaded data might be automatically analyzed for patterns, and if pre-set patterns are detected, then a report or alert might be generated (for example, to a supervisor who might then manage or address the issue). By way of example of such pattern analysis, if the noise exposure measurement (of a QuietPro device, for example) from the worker's two ears is significantly different (for example, the two sensors/inner microphones of a QuietPro™-type device detect significantly different protected noise levels), this may be indicative of an issue that should be investigated (for example, malfunctioning equipment or improper use of equipment due to improper training). Or if the same PPE device 104, when used by more than one employee, reports exposure incidents, then the PPE device 104 might be flagged to be checked for malfunction. Or if a specific worker 114 is reported as having multiple exposure incidents when using several different PPE devices 104, then the worker 114 might be flagged for additional training. A supervisor might consider the pattern information report (which may include specific recommendations automatically generated by computer, depending on the detected pattern) and communicate or signal the need to check for malfunctions (e.g. defective PPE equipment) and/or schedule additional training for the worker 114, for example. In other embodiments, such follow-up after a detected pattern might be performed entirely automatically (for example, by a computer such as the terminal server 110). Another example of information analysis might be repeated exposure by the worker 114 over the limit/threshold, which might indicate a need to reconfigure the PPE 104, to re-train the worker 114 in effectively using the PPE 104, or to rework the schedule to remove the worker 114 from dangerous exposure zones. Another example of utilizing such analyzed data might be if multiple workers 114 in the same work zone 112 are all over their limit/threshold. This might indicate a need to consider ways to lower exposure in that work zone 112, for example. Additionally, the PPE data might be used, perhaps in conjunction with the worker's other personal information, to determine an appropriate length of time for recuperation in a safe zone or recuperation zone 118, and may assist in scheduling the worker 114 based on exposure history.

In some instances, the one or more kiosks 102 might also measure general exposure levels at the particular work zone 112 location (for example, having a microphone for detecting background noise levels, or other sensor(s) for detecting the relevant exposure information for the general work zone 112). In such systems, the kiosk 102 might provide additional information to the terminal server for analysis and reporting.

Figure 6:
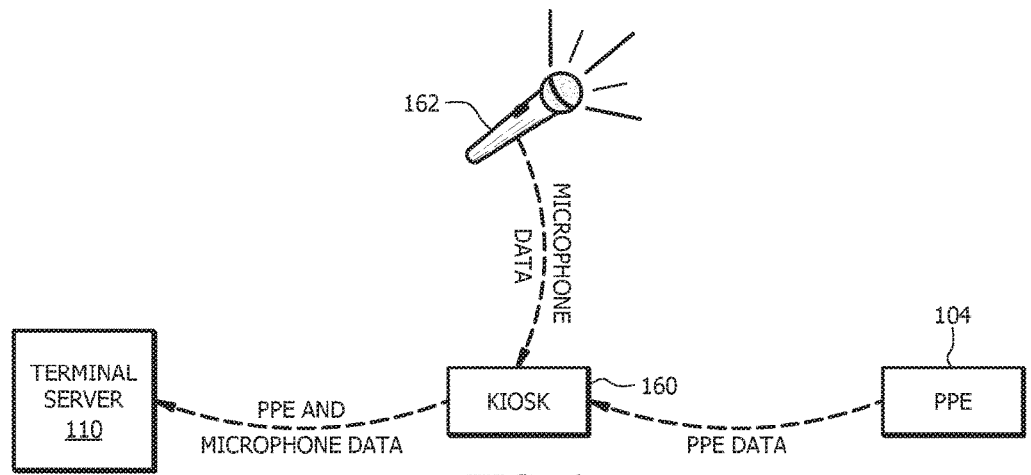
FIG. 6 illustrates schematically an exemplary system according to an embodiment of the disclosure in which the kiosk is operable to record the local conditions at a work zone (for example, using a microphone to record noise exposure), such that the kiosk may upload/transmit its own data along with the PPE data uploaded from the PPE.

FIG. 6 illustrates such an exemplary embodiment (which might typically be configured for use with hpd PPE, such as QuietPro), in which the kiosk 160 records the general background noise level at the work zone/site (for example, using a microphone 162). Then the kiosk 160 may transmit both the PPE data and the kiosk information (e.g. microphone data) to the terminal server 110 (to be associated with the worker's personal information in the database, for example). Such general exposure information could further aid in scheduling for example (e.g. helping a supervisor schedule workers with recent exposure over the limit to work zones 112 that historically have lower exposure, in order to further aid recuperation by the worker 114). And in some embodiments, a plurality of kiosks 160 might each detect general exposure, while also tracking the worker's movement (by for example, tracking the location of the PPE 104 whenever the PPE 104 passes in proximity to one of the kiosks 160). This movement/location data might also be helpful in helping to set future schedules for the worker 114 (by for example, showing the location where any exposure incidents have occurred). Furthermore, such location data might also be helpful in considering plant maintenance (for example, the need to take corrective action/repairs at one or more location in the plant in an attempt to reduce general exposure, thereby reducing exposure incidents for specific workers 114).

Some systems might further include sensors at a work zone 112 operable to automatically check the identity of the worker 114 and/or proper positioning of the PPE device 104. So for example, such sensors might include visual verification devices, such as one or more cameras, for use with facial recognition (e.g. to identify the worker) and/or for ensuring that PPE 104 is positioned at the proper location on the worker 114. Such sensors would typically be located at access points to work zones 112 requiring PPE 104 (for example, at a door, gate, or other entrance) and/or at the location of specific equipment requiring PPE 104.

Figure 7:
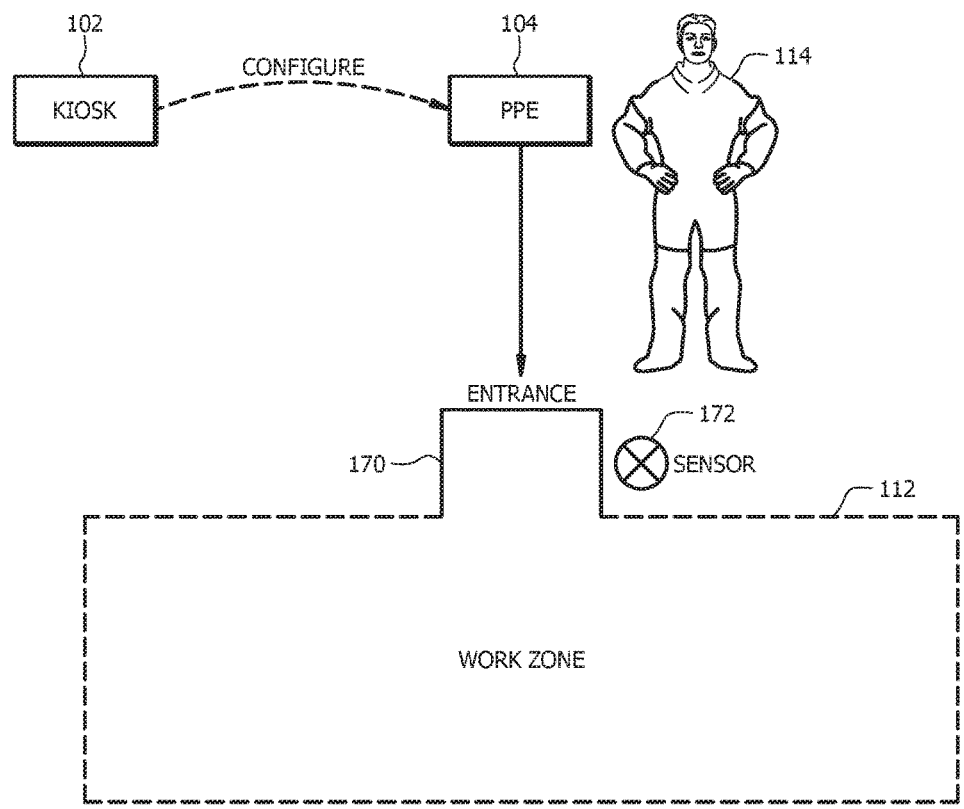
FIG. 7 illustrates schematically an exemplary system according to an embodiment of the disclosure in which a kiosk may configure a PPE for a worker (for example, using the worker's personal information), and then additionally, one or more sensors located with respect to a work zone (for example, at an entrance to the work zone) might check/verify the worker's identity and/or PPE positioning/use prior to the worker entering the work zone.

FIG. 7 illustrates such an exemplary system. In FIG. 7, the kiosk 102 might associate and configure the PPE 104 for the worker 114 based on the worker-specific personal information (as described above, for example). In some embodiments, the kiosk 102 might also generally check the worker's personal information to determine if the worker 114 is trained to use the required PPE 104, if the worker 114 is authorized to enter the work zone 112 (for example, based on job functions), and/or if the worker 114 has any medical issues that would preclude the worker 114 entering the work zone 112 and/or using the PPE 104. By way of example, if the worker 114 has not passed training for the particular PPE 104, then the worker's file might be flagged to recommend or schedule training. Or if the worker 114 is not authorized to enter the work zone 112, the PPE 104 might not be assigned and/or entry might be denied. Or if the worker 114 has a medical issue incompatible with the required PPE 104, then the PPE 104 might be refused (e.g. not provided or assigned) and/or a warning might be issued (for example, by the kiosk 102). If the worker 114 does not pass any of the checks, then the PPE 104 would typically not be assigned/provided or associated (and/or a warning might be provided).

If the worker 114 passes the checks and is assigned PPE 104, then the second part of the system of FIG. 7 (which is typically located at an entrance 170 to the work zone 112 requiring PPE 104 and/or at a location of equipment requiring PPE 104) might employ sensors 172 (such as one or more cameras or other identifying devices associated with/linked to/interacting with a computer configured with software to perform checks) to check the worker's identity (for example, using facial recognition software and/or requiring entry of PIN number and/or access card and/or fingerprint and/or eye scan, etc.) and/or to check to see if the PPE 104 is present (for example, using RFID) and/or is properly located on the user's person (see for example, Honeywell U.S. patent application Ser. No. 13/452,596, hereby incorporated by reference to the extent that it does not conflict with specific information herein). So for example, the entrance 170 might have a door or gate which will not open unless the one or more checks by the sensor(s) 172 are successful (e.g. the sensor check determines if the entrance 170 is automatically unlocked or otherwise actuated to allow entry). While this might be performed by a processor located at the entrance 170, in some embodiments the kiosk 102 would be in communication with the entrance 170 and might receive the sensor data and/or control the locking mechanism of the entrance 170. And in some embodiments, some or all of the personal information from the kiosk 102 might also be communicated to the entrance 170 of the work zone 112, so that the worker 114 might not be allowed to enter work zones 112 for which his medical condition, for example, might preclude or advise against entrance. In some embodiments, multiple compliance systems might also be used in conjunction, to prevent false alerts. So for example, facial recognition might be used at the kiosk 102 to verify the worker's identity in conjunction with the worker 114 inputting a corresponding PIN number and/or ID card. Thus, the system might automate compliance checks.

In some embodiments, the kiosk 102 might effectively track the actual time that PPE 104 has been in use (for example, based on the difference between check-out time and check-in time and/or by using a timer device on the PPE 104 that activates when the PPE 104 is in use and deactivates when the PPE 104 is not in use, thereby keeping a running tally of operation time for the PPE 104 which might be reported to the kiosk 102). This PPE data might allow for more effective monitoring of PPE life (for replacement) and/or maintenance needs, and reports might be automatically generated to schedule maintenance for such PPE devices 104. Such PPE data relating to life and/or maintenance might also be uploaded to the terminal server 110 (for example, kept in a spate database correlating PPE devices 104 to a maintenance or decommissioning schedule), which might then allow for searches, reports, and/or automated scheduling of recommended tasks for each specific PPE 104 based on its own actual run-time (usage) information.

In some instances, the training issue might also relate to job functions for the worker 114 (since for example, if the job function of the worker 114 has changed, then training may need to be evaluated at that stage as well, and a recommendation might automatically be issued to schedule training (for example, in an attempt to ensure proper training as soon as possible, rather than waiting until the worker 114 requests PPE 104 for which he is not trained)). Thus, the terminal server 110 might map within its database a worker 114 to a job (and the related job functions) and to the worker's current/actual training status (for PPE 104 for example), which in turn might be mapped to training requirements (for the job or PPE 104) and/or to the PPE 104 used for that job. So for instance, when a worker 114 changes jobs, the worker's personal information might be updated to the new job, which then would be linked to specific training as required for that new job. By comparing the worker's actual training data/history to the requirements for the new job, training compliance might typically be achieved at an early stage (rather than catching non-compliance only as the PPE 104 is improperly requested). Similarly, if the regulations change the PPE requirements for a job, such a system would allow for early identification of the need to train workers 114 based on updated PPE regulations. Also, if the worker 114 had previously been trained for a PPE device 104, but that training was sufficiently distant in the past so that new/refresher training is needed to ensure that the worker 114 is up-to-date on the training requirements (e.g. the worker's training is not out-of-date), then the worker 114 might be flagged by the system automatically. Once training issues have been flagged, the system might automatically recommend and/or schedule additional training to ensure compliance. Such a system might ensure that training certifications are kept current, automatically catching any discrepancies at an early stage (rather than waiting to catch the discrepancy only at the compliance check when PPE 104 is requested).

Some system embodiments might also include a feedback system (which could be located in the kiosk 102 in some embodiments). For example, the feedback system might use a dynamic questionnaire, and the worker's personal information might be used by the system to select appropriate questions for such a questionnaire (for example, based on job functions, PPE associations, work zones, etc.). Typically, such a questionnaire would be dynamic, with questions being selected in an on-going manner throughout the process based on the worker's personal information and/or the worker's earlier answers to prior questions in the questionnaire. Such feedback from the worker 114 typically would be uploaded to the terminal server 110 and associated with the worker's personal information. The feedback might also be used to generate reports. For example, supervisors might use the information to monitor issues and take corrective action based on recurring complaints or suggestions. And in some embodiments, feedback sessions might be regularly scheduled. For example, feedback sessions might be scheduled on a periodic basis and/or based on personal information (for example, if the personal information indicates that the worker has a new job function or that the worker has had exposures).

Figure 8A:
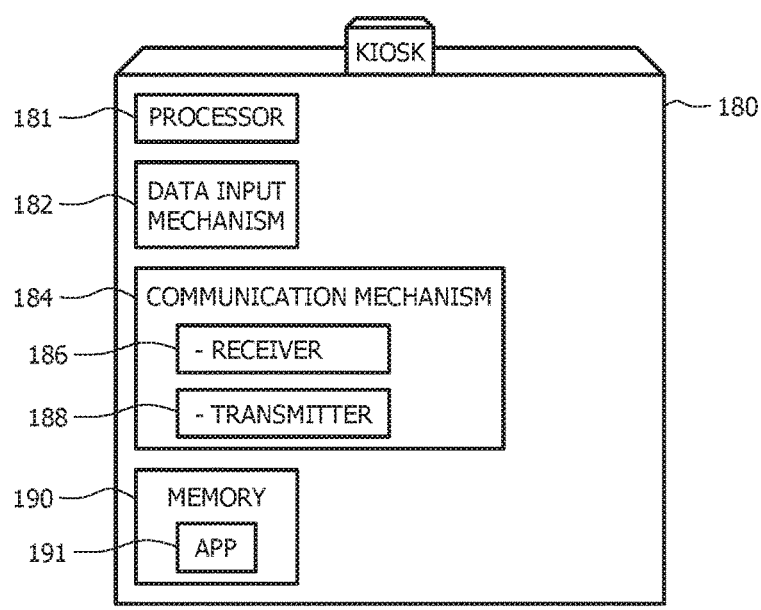
Figure 8B:
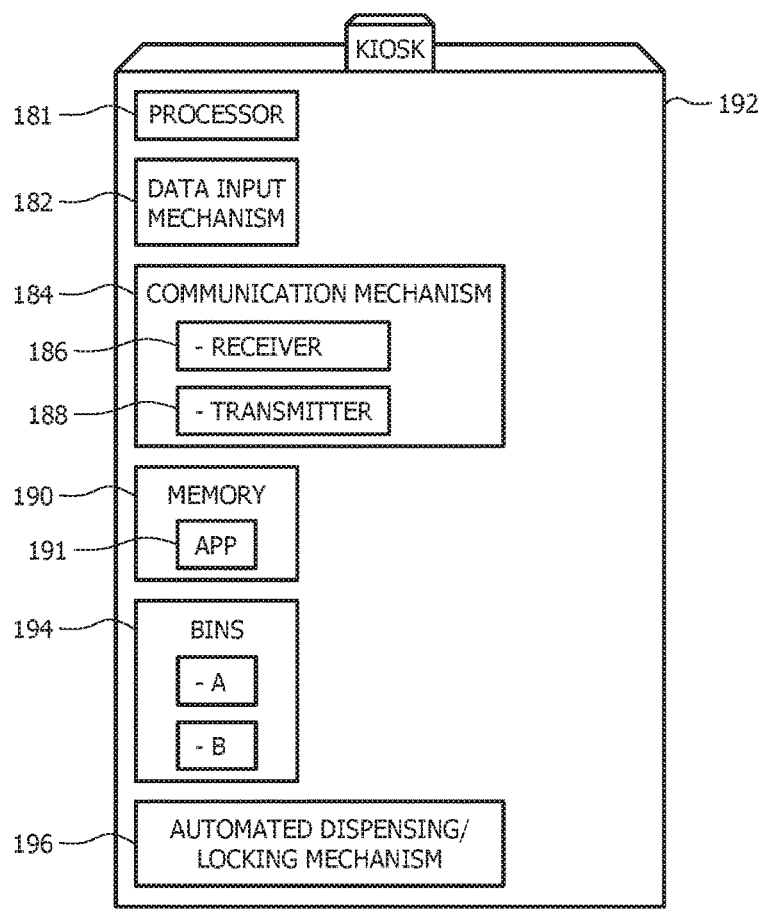
FIG. 8B illustrates schematically a second exemplary kiosk embodiment.

FIGS. 8A and 8B illustrate two different exemplary kiosks 180, 192 embodiments, for example, of the sort that might be used in the embodiments of FIGS. 1, 2, 3, 5, 6, and 7. The embodiment of FIG. 8B might also be used with the system embodiment of FIG. 4 (since for example, it includes a plurality of bins 194). The example kiosks 180, 192 of FIGS. 8A and 8B are merely possible illustrative kiosk embodiments, and other kiosk embodiments may include additional elements and/or delete one or more listed element (for example, depending upon the system configuration and/or type of PPE 104). In some embodiments, one or more listed element might be located separately (for example, accessed remotely). The kiosk of FIG. 8A comprises a processor 181, a data input mechanism 182 (such as a keypad, touchscreen, camera/sensor, microphone with voice recognition software, scanner, etc.), a communication mechanism 184 (which might for example, include a receiver 186 and/or transmitter 188), a memory storage 190, and a kiosk application 191 stored in the memory storage 190. In some contexts, the memory storage 190 may be referred to as a non-transitory memory, for example, a memory storage that retains its contents after electrical power is removed from the memory storage. The kiosk application 191 comprises computer instructions that, when executed by the processor 181, provide the automated processing performed by the kiosk 180 described above. In some embodiments, the communication mechanism 184 may include two different communication means (for example, with one configured for communication with PPE 104 (for example, using Bluetooth or other short-range wireless) and one configured for communication with a terminal server 110 (for example, over a cloud network, using long range wireless, and/or using a direct connection means)). And in some embodiments, the data input mechanism 182 might include two different data input devices (for example, with one configured for entry of worker unique identifier information and another configured for PPE unique identifier information). In another embodiment, however, a single data input mechanism 182 (such as a keypad or voice recognition system) might allow entry of both such types of information.

The embodiment of FIG. 8B is similar to that of FIG. 8A, but also includes a plurality of bins 194, each holding one or more of a specific PPE device 104, and an automated dispensing and/or locking/unlocking mechanism 196 (for example, operable to automatically dispense a PPE device 104 from the appropriate bin 194 (for example, at the control of the processor 181)). It is understood that the kiosk application 191 of FIG. 8B may differ from the kiosk application 191 of FIG. 8A by further providing computer instructions for controlling the automated dispensing and/or locking/unlocking mechanism 196.

Figure 9:
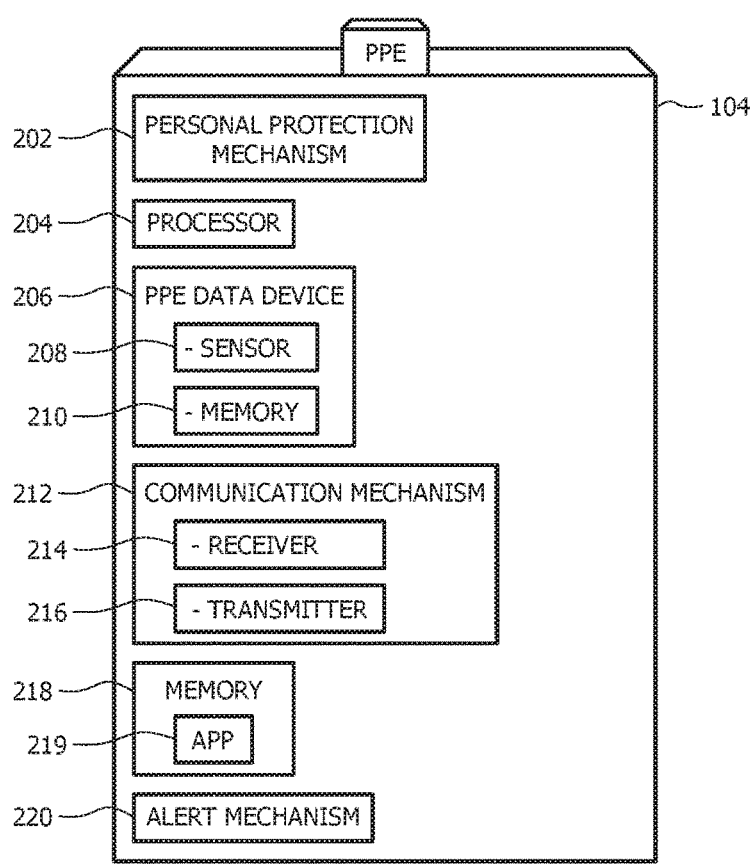
FIG. 9 illustrates schematically (in a block diagram) an exemplary PPE device embodiment.

FIG. 9 illustrates an exemplary PPE 104 embodiment, for example, of the sort that might be used in the embodiments of FIGS. 1-7. The example PPE 104 of FIG. 9 is merely one possible illustrative PPE embodiment, and other PPE embodiments may include additional elements and/or delete one or more listed element (for example, depending upon the system configuration). In some embodiments, one or more listed element might be located separately (for example, accessed remotely). The PPE 104 of FIG. 9 comprises a personal protection mechanism 202 (e.g. the element that actually protects the worker 114 from exposure, for example, a hearing protection device), a processor 204, a PPE data device 206 (for example, a noise exposure monitoring component), which might for example, have a sensor 208 (for example, a microphone) coupled to memory storage 210 (for example, allowing the PPE data device to record noise exposure data), a communication mechanism 212 (which might typically include a receiver 214 and/or a transmitter 216), a memory storage element 218 (for example, configured/operable to store the personal information downloaded from the kiosk 102, 180, 192, so that the processor 204 may use the stored personal information and/or personal information derivative data to automatically analyze the PPE data and to automatically trigger/control an alarm warning of exposure), a PPE application 219 stored in the memory storage element 218, and an alert mechanism 220 (for example, which might be activated by the processor 204 to provide an audio and/or visual alert if exposure is over the pre-set limit). Some embodiments may have only a single memory element, which might be shared so that a portion of the memory 218 is used to record PPE data, while another portion of the memory 218 might be used to store configuration information from the kiosk 102, 180, 192 (for example, a personal noise exposure limit). The PPE application 219 comprises computer instructions that, when executed by the processor 204, provides the automated processing performed by the PPE 104, for example recording PPE data, uploading and/or transmitting PPE data to the kiosk 102, 180, 192, downloading configuration information from the kiosk 102, 180, 192, and configuring the PPE 104 based on the downloaded configuration information, for example configuring alarm limits.

Figure 10:
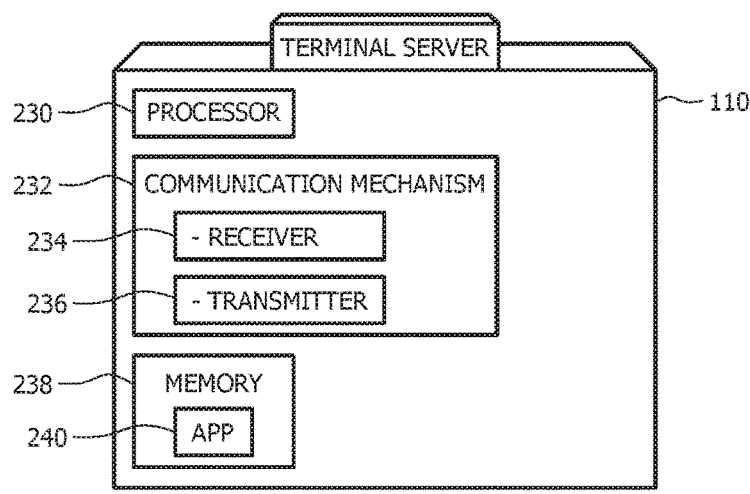
FIG. 10 illustrates schematically (in a block diagram) an exemplary terminal server embodiment.

FIG. 10 illustrates an exemplary terminal server 110 embodiment, for example, of the sort that might be used in the embodiments of FIGS. 2, 3, 4, 5, 6, and optionally 7. The example terminal server 110 of FIG. 10 is merely one possible illustrative terminal server embodiment, and other terminal server embodiments may include additional elements and/or delete one or more listed element (for example, depending upon the system configuration). In some embodiments, one or more listed element might be located separately (for example, accessed remotely). The terminal server 110 of FIG. 10 comprises a processor 230, a communication mechanism 232 (which typically might include a receiver 234 and/or a transmitter 236), a memory storage 238, and a server application 240 stored in the memory storage 238. In some contexts, the memory storage 238 may be referred to as a non-transitory memory. The server application 240 comprises computer instructions that, when executed by the processor 230, provides the automated processing performed by the terminal server 110 described above. While in some embodiments the memory 238 might house a plurality of worker files (e.g. a database), each having personal information relating to a specific worker 114 (in addition to having space to store information for use by the processor 230 when receiving queries from the kiosk(s) 102, 180, 192 and/or transmitting information to the kiosk(s) from the database), in other embodiments the database of worker personal information might be an external unit, which the terminal server 110 might access, for example, remotely. If the terminal server 110 is a cloud server, then it might operate over a cloud network, for example.

In the device embodiments of FIGS. 8-10, a subset of the listed components/elements (e.g. less than all of the listed components/elements) and/or additional components/elements not listed may be included in the device. The processor (or some other form of controller or central processing unit) typically operates to control the various components of the device, for example, in accordance with embedded software or firmware stored in memory or stored in memory contained within the processor itself. In addition to the embedded software or firmware, the processor may execute other applications stored in memory or made available via information carrier media such as portable data storage media like a removable memory card or via wired or wireless network communications. The application software may comprise a compiled set of machine-readable instructions that configure the processor to provide the desired functionality, or the application software may be high-level software instructions to be processed by an interpreter or compiler to indirectly configure the processor. In some embodiments, the communications mechanism of the device might comprise a Bluetooth interface or an IEEE 802.11 compliant wireless interface which may enable the device to communicate wirelessly with other nearby devices. Some device embodiments may use a keypad as a data input mechanism, allowing a user to make selections, enter information, and otherwise provide input to the device. Another such input mechanism might be a touch screen LCD.

Systems of the present disclosure may include a software environment that may be implemented by the processor of the one or more devices. The processor may execute operating system software that provides a platform from which the rest of the software operates. The operating system may provide a variety of drivers for the hardware with standardized interfaces that are accessible to application software. The operating system software may be coupled to and interact with application management services (AMS) that transfer control between applications running on a remote device. A system may further comprise a portal application for coupling to a remote computing device. Some portions of the system described may be implemented by a computer system(s) with sufficient processing power, memory resources, and network throughput capacity to handle the necessary workload placed upon it. Memory elements may include non-transitory memory, read only memory (ROM), and/or random access memory (RAM). The processor(s) of devices may be implemented as one or more CPU chips.

It is understood that by programming and/or loading executable instructions onto the computer system (e.g. a computerized device), at least one of the CPU, the RAM, and the ROM may be changed, transforming the computer system into a particular machine or apparatus (e.g. a specialized computer) having novel functionality, for example, as taught by the present disclosure. It is fundamental to the electrical engineering and software engineering arts that functionality that can be implemented by loading executable software into a computer can be converted to a hardware implementation by well-known design rules. Decisions between implementing a concept in software versus hardware typically hinge on considerations of stability of the design and numbers of units to be produced rather than any issues involved in translating from the software domain to the hardware domain. Generally, a design that is still subject to frequent change may be preferred to be implemented in software, because re-spinning a hardware implementation is more expensive than re-spinning a software design. Generally, a design that is stable that will be produced in large volume may be preferred to be implemented in hardware, for example, in an application-specific integrated circuit (ASIC), because for large production runs the hardware implementation may be less expensive than the software implementation. Often a design may be developed and tested in a software form and later transformed, by well-known design rules, to an equivalent hardware implementation in an application specific integrated circuit that hardwires the instructions of the software. In the same manner as a machine controlled by a new ASIC is a particular machine or apparatus, likewise a computer that has been programmed and/or loaded with executable instructions may be viewed as a particular machine or apparatus.

Additionally, after the computer system is turned on or booted, the processor (e.g. central processing unit (CPU)) may execute a computer program or application. For example, the CPU may execute software or firmware stored in the ROM or stored in the RAM. In some cases, on boot and/or when the application is initiated, the CPU may copy the application or portions of the application from secondary storage to the RAM or to memory space within the CPU itself, and the CPU may then execute instructions that the application is comprised of. In some cases, the CPU may copy the application or portions of the application from memory accessed via the network connectivity devices or via the I/O devices to the RAM or to memory space within the CPU, and the CPU may then execute instructions that the application is comprised of. During execution, an application may load instructions into the CPU, for example, load some of the instructions of the application into a cache of the CPU. In some contexts, an application that is executed may be said to configure the CPU to do something, e.g., to configure the CPU to perform the function or functions promoted by the subject application (for example, as discussed above). When the CPU is configured in this way by the application, the CPU becomes a specific purpose computer or a specific purpose machine.

Any secondary storage typically would be comprised of one or more disk drives or tape drives and is used for non-volatile storage of data and as an over-flow data storage device if RAM is not large enough to hold all working data. Secondary storage may be used to store programs which are loaded into RAM when such programs are selected for execution. The ROM is used to store instructions and perhaps data which are read during program execution. ROM is a non-volatile memory device which typically has a small memory capacity relative to the larger memory capacity of secondary storage. The RAM is used to store volatile data and perhaps to store instructions. Access to both ROM and RAM is typically faster than to secondary storage. The secondary storage, the RAM, and/or the ROM may be referred to in some contexts as computer readable storage media and/or non-transitory computer readable media.

While only one processor might be shown for a device, multiple processors may in fact be present in some embodiments. Thus, while instructions may be discussed as executed by a processor, the instructions may be executed simultaneously, serially, or otherwise executed by one or multiple processors. In an embodiment, the computer system (e.g. one or more computerized devices) may comprise two or more computers in communication with each other that collaborate to perform a task. For example, but not by way of limitation, an application may be partitioned in such a way as to permit concurrent and/or parallel processing of the instructions of the application. Alternatively, the data processed by the application may be partitioned in such a way as to permit concurrent and/or parallel processing of different portions of a data set by the two or more computers. So, for example, the terminal server might actually be implemented as a plurality of computers in communication. In an embodiment, virtualization software may be employed by the computer system to provide the functionality of a number of servers that is not directly bound to the number of computers in the computer system. For example, virtualization software may provide twenty virtual servers on four physical computers. In an embodiment, the functionality disclosed above may be provided by executing the application and/or applications in a cloud computing environment. Cloud computing may comprise providing computing services via a network connection using dynamically scalable computing resources. Cloud computing may be supported, at least in part, by virtualization software. A cloud computing environment may be established by an enterprise and/or may be hired on an as-needed basis from a third party provider. Some cloud computing environments may comprise cloud computing resources owned and operated by the enterprise as well as cloud computing resources hired and/or leased from a third party provider.

In an embodiment, some or all of the functionality disclosed above may be provided as a computer program product. The computer program product may comprise one or more computer readable storage medium having computer usable program code embodied therein to implement the functionality disclosed above. The computer program product may comprise data structures, executable instructions, and other computer usable program code. The computer program product may be embodied in removable computer storage media and/or non-removable computer storage media. The removable computer readable storage medium may comprise, without limitation, a paper tape, a magnetic tape, a magnetic disk, an optical disk, a solid state memory chip (for example, analog magnetic tape), compact disk read only memory (CD-ROM) disks, floppy disks, jump drives, digital cards, multimedia cards, and others. The computer program product may be suitable for loading, by the computer system, at least portions of the contents of the computer program product to the secondary storage, to the ROM, to the RAM, and/or to other non-volatile memory and volatile memory of the computer system. The processor may process the executable instructions and/or data structures in part by directly accessing the computer program product, for example, by reading from a CD-ROM disk inserted into a disk drive peripheral of the computer system. Alternatively, the processor may process the executable instructions and/or data structures by remotely accessing the computer program product, for example, by downloading the executable instructions and/or data structures from a remote server through the network connectivity devices. The computer program product may comprise instructions that promote the loading and/or copying of data, data structures, files, and/or executable instructions to the secondary storage, to the ROM, to the RAM, and/or to other non-volatile memory and volatile memory of the computer system.

In some contexts, the secondary storage, the ROM, and the RAM may be referred to as a non-transitory computer readable medium or a computer readable storage media. A dynamic RAM embodiment of the RAM, likewise, may be referred to as a non-transitory computer readable medium (e.g., flash random access memory (FRAM) that is not reliant on power to retain information) in that while the dynamic RAM receives electrical power and is operated in accordance with its design, for example, during a period of time during which the computer system is turned on and operational, the dynamic RAM stores information that is written to it. Similarly, the processor may comprise an internal RAM, an internal ROM, a cache memory, and/or other internal non-transitory storage blocks, sections, or components that may be referred to in some contexts as non-transitory computer readable media or computer readable storage media.

Having described above various system embodiments (especially those shown in the figures), various alternative system embodiments may include, but are not limited to, the following:

In a first embodiment, a system comprising: a computerized kiosk; and a personal protective equipment ("PPE") device (although in other embodiments, the PPE might not be an actual part of the claimed system, but rather the system might simply be configured to interact with such a (or one or more) PPE device, which is also included within this embodiment as an alternative); wherein the kiosk is operable to associate the PPE with personal information of a worker. In a second embodiment, the system of embodiment 1 wherein the kiosk is operable to configure the PPE based on the personal information, so that the PPE better suits the worker who will be using the PPE. In a third embodiment, the system of embodiment 2 wherein configuring the PPE comprises actively changing the PPE. In a fourth embodiment, the system of embodiments 2-3 wherein the PPE comprises a hearing protection device ("hpd") and a noise exposure monitoring component; and wherein configuring the PPE comprises setting the personal sound exposure limit for the noise exposure monitoring component using the personal information of the worker. In a fifth embodiment, the system of embodiments 2-4 wherein configuring the PPE comprises (or further comprises) determining the appropriate PPE based on the worker's personal information, and only associating/assigning/providing the PPE to the worker if the PPE is appropriate based on the worker's personal information. In a sixth embodiment, the system of embodiments 2-5 wherein the kiosk comprises storage bins having multiple types of PPE (typically multiple types of PPE from the same category of PPE); and wherein configuring the PPE comprises the kiosk automatically providing (and associating) the appropriate type of PPE from the storage bins to the worker based on the personal information of the worker. In a seventh embodiment, the system of embodiments 1-6 wherein the kiosk is operable to upload PPE information from the PPE. In an eighth embodiment, the system of embodiments 1-7 wherein the kiosk is one of a plurality of kiosks, and wherein each of the plurality of kiosks is operable to communicate with a terminal server. In a ninth embodiment, the system of embodiment 8 wherein in order to associate the PPE with the personal information of the worker, the kiosk downloads the personal information of the worker from the terminal server. In a tenth embodiment, the system of embodiments 7-9 wherein upon uploading PPE information from the PPE, the kiosk automatically uploads the PPE information to the terminal server (to be included in the worker's personal information). In an eleventh embodiment, the system of embodiments 7-10 wherein the terminal server and/or the kiosk automatically searches for patterns in the uploaded PPE information (and/or automatically reports any such detected patterns). In a twelfth embodiment, the system of embodiments 7-10 wherein the terminal server and/or kiosk automatically recommends future scheduling for the worker, based on the personal information (e.g. including the PPE information). In a thirteenth embodiment, the system of embodiments 1-12 wherein personal information comprises one of the following: a personal sound/noise exposure limit (for example, based on hearing tests and or exposure history), personalized default volume setting, information regarding exposure history, information on job functions/tasks, information on authorized work zones, information on training requirements and records, information on medical history/flags, information on job history, and combinations thereof. In a fourteenth embodiment, the system of embodiments 1-13 wherein before the PPE is associated/assigned to, provided to the worker, the kiosk checks at least the following personal information: training records/status and/or medical records/flags. In a fifteenth embodiment, the system of embodiments 4-14 wherein the noise exposure monitoring component is operable to record protected noise exposure (e.g. noise exposure under the hpd), and is operable to warn the worker if protected noise exposure exceeds a pre-set limit; wherein the pre-set limit is the personal sound exposure limit. In a sixteenth embodiment, the system of embodiments 4-15 wherein the PPE and noise exposure monitoring component are integrated into a single PPE device. In a seventeenth embodiment, the system of embodiments 4-16 wherein the PPE further comprises a sound pass-through component (e.g. an external microphone and a speaker under the hpd, operable to transmit external sound through to the user) and/or a wireless communication component (e.g. radio communication device) (with a receiver and speaker under the hpd, operable to transmit a communication broadcast into the worker's ear under the hpd), and wherein configuring the PPE further comprises setting the default volume level for the PPE (e.g. the sound pass-through component and/or wireless communication component). In an eighteenth embodiment, the system of embodiments 4-17 wherein the kiosk is operable to upload the recorded noise exposure data from the PPE. In a nineteenth embodiment, the system of embodiments 1-18 wherein the kiosk is one of a plurality of kiosks; wherein each of the plurality of kiosks is operable to communicate with a terminal server; wherein in order to associate the PPE with the personal information of the worker, the kiosk downloads the personal information of the worker from the terminal server; and/or wherein upon uploading recorded noise exposure data from the PPE, the kiosk automatically uploads the recorded noise exposure data to the terminal server (for example, to be included in the worker's personal information). In a twentieth embodiment, the system of embodiments 8-19 wherein the terminal server automatically searches for patterns in the uploaded PPE information (and automatically reports any such detected patterns). In a twenty-first embodiment, the system of embodiment 20 wherein one such pattern comprises noise exposure data from the two ears of the worker that does not substantially match. In a twenty-second embodiment, the system of embodiments 1-21 wherein the kiosk is operable to measure local noise levels; and/or wherein the terminal server and/or kiosk automatically recommends future scheduling for the worker, based on the personal information (for example, including the recorded noise exposure data).

Also, having described above various method embodiments (especially those discussed in relation to the system embodiments shown in the figures and/or described above), various alternative method embodiments may include, but are not limited to, the following:

In a first method embodiment, a method comprising: associating personal information of a worker (which is typically stored in a database) with a personal protective equipment ("PPE") device using a computerized kiosk (wherein the database typically might be accessible via the kiosk, for example, the database might be located on the kiosk or located on a terminal server in communication with the kiosk). In a second method embodiment, the method of embodiment 1, wherein the personal information comprises one or more of the following: a personal sound/noise exposure limit (for example, based on hearing tests and or exposure history), personalized default volume setting, information regarding exposure history, information on job functions/tasks, information on authorized work zones, information on training requirements and records, information on medical history/flags, information on job history. In a third method embodiment, the method of embodiments 1-2, wherein the personal information of the worker is located in a database on a terminal server, the method further comprising downloading the personal information from the terminal server to the kiosk. In a fourth method embodiment, the method of embodiments 1-3, wherein downloading the personal information comprises providing the kiosk with worker identification information and with PPE identification information (e.g. serial number), and wherein the kiosk uses the worker identification information to request personal information from the terminal server database (and wherein in response to such request, the terminal server associates the personal information of the worker in the database with the PPE (using the PPE identification number, for example) and/or downloads the requested personal information to the kiosk). In a fifth method embodiment, the method of embodiments 1-4, further comprising configuring the PPE using the personal information (e.g. the kiosk configures the PPE using the personal information, so that the PPE may better suit the worker who will be using (e.g. assigned) the PPE). In a sixth method embodiment, the method of embodiment 5, wherein configuring the PPE comprises actively changing the PPE. In a seventh method embodiment, the method of embodiment 6, wherein the PPE is a hearing protection device with noise exposure monitoring, and wherein actively changing the PPE comprises setting the noise exposure limit for the hearing protection device with noise exposure monitoring using the personal information of the worker who will be using/assigned the PPE. In an eighth method embodiment, the method of embodiment 5, wherein configuring the PPE comprises providing PPE based on the personal information (e.g. determining the appropriate PPE based on the worker's personal information and only associating or providing the PPE to the worker if the PPE is appropriate based on the worker's personal information). In a ninth method embodiment, the method of embodiment 8, wherein the kiosk comprises a plurality of storage bins, each having one of a plurality of types of PPE (for example, typically a plurality of types of PPE from the same category of PPE); and wherein providing PPE comprises (the kiosk) automatically providing the appropriate type of PPE from the plurality of storage bins to the worker based on the personal information of the worker. In a tenth method embodiment, the method of embodiment 5, wherein configuring the PPE comprises refusing to provide or assign the PPE to the worker based on personal information (for example, in the event that the personal information indicates that the PPE is not appropriate for the worker). In an eleventh method embodiment, the method of embodiments 1-10, further comprising uploading PPE information from the PPE to the kiosk (for example, using the kiosk to upload PPE information). In a twelfth method embodiment, the method of embodiment 11, wherein PPE information comprises data recorded/measured by the PPE during usage by the worker (for example, during a shift—such that PPE information might be uploaded to the kiosk after the work shift). In a thirteenth method embodiment, the method of embodiments 11-12, further comprising uploading the PPE information from the kiosk to the terminal server (and associating/including the PPE information with the personal information in the database). In a fourteenth method embodiment, the method of embodiments 11-13, further comprising associating/including the PPE information with the personal information in the database. (e.g. using the PPE information to update the personal information of the worker to whom the PPE has been assigned/associated). In a fifteenth method embodiment, the method of embodiments 11-14, further comprising searching the personal information (for example, the PPE information) on the database to detect one or more pre-set patterns. In a sixteenth method embodiment, the method of embodiment 15, wherein the pattern includes one or more of the following: a significant difference between simultaneous PPE measurements/recordings, exposure incidents by multiple workers using the same PPE device (at discrete times), multiple exposure incidents by a worker using different PPE devices (over time), repeated exposures over the limit by a worker, and/or multiple workers using different PPE devices being exposed over the limit (for example, simultaneously). In a seventeenth method embodiment, the method of embodiment 16, wherein upon detection of a pattern, an alert is generated (for example, the kiosk might notify the worker, or a report might be sent to the computer or smart phone of the worker's supervisor). In an eighteenth method embodiment, the method of embodiments 14-17, further comprising scheduling the worker's future work based on the personal information (e.g. using the personal information to automatically recommend a schedule for the worker). In a nineteenth method embodiment, the method of embodiments 1-18, further comprising using the personal information to verify compliance at a point of entry (e.g. entrance) to a work zone (e.g. having sensors located at the entrance to the work zone, and the sensors using the personal information to check compliance and to either grant or deny access or provide an alert). In a twentieth method embodiment, the method of embodiments 1-19, wherein before the PPE is assigned/provided to the worker, the kiosk checks at least the following personal information of the worker: training records/status and/or medical records/flags. In a twenty-first method embodiment, the method of embodiments 7-20, wherein the hearing protection device further comprises sound pass-through and/or wireless communication, and wherein configuring the hearing protection device further comprises setting a default volume level for the hearing protection device. In a twenty-second method embodiment, the method of embodiments 7-21, further comprising uploading (e.g. to the kiosk and/or the terminal server, for example, into the database to be included within the personal information) recorded noise exposure data from the PPE (e.g. the PPE information comprises noise exposure data). In a twenty-third method embodiment, the method of embodiment 22, further comprising automatically searching for a pattern comprising noise exposure data from the two ears of the worker (e.g. the two sites of the hpd) that does not substantially match (e.g. identifying whenever the noise exposure data from the two ears differs significantly enough to indicate an issue, such as a likely malfunction of the hpd and/or improper use/fit of the hpd by the worker). In a twenty-fourth method embodiment, the method of embodiments 15-23, further comprising automatically recommending future scheduling of the worker based on the personal information (including for example, the recorded noise exposure data and/or any additional noise measurement data from other sources—such as the kiosk(s)).

Persons of skill will understand and appreciate that described systems and methods may inter-relate, such that descriptions relating to a system may be relevant (and included in) descriptions of methods herein, and vice versa.

While various embodiments in accordance with the principles disclosed herein have been shown and described above, modifications thereof may be made by one skilled in the art without departing from the spirit and the teachings of the disclosure. The embodiments described herein are representative only and are not intended to be limiting. Many variations, combinations, and modifications are possible and are within the scope of the disclosure. Alternative embodiments that result from combining, integrating, and/or omitting features of the embodiment(s) are also within the scope of the disclosure. Accordingly, the scope of protection is not limited by the description set out above, but is defined by the claims which follow, that scope including all equivalents of the subject matter of the claims. In the disclosure, any designation of a claim or embodiment as depending from a range of claims or embodiments (for example, #-##) would indicate that the claim or embodiment is multiple dependent based on any claim or embodiment in the range (e.g. dependent on claim/embodiment # or claim/embodiment ## or any claim/embodiment therebetween). Each and every claim is incorporated as further disclosure into the specification and the claims are embodiment(s) of the present invention(s). Furthermore, any advantages and features described above may relate to specific embodiments, but shall not limit the application of such issued claims to processes and structures accomplishing any or all of the above advantages or having any or all of the above features.

Additionally, the section headings used herein are provided for consistency with the suggestions under 37 C.F.R. 1.77 or to otherwise provide organizational cues. These headings shall not limit or characterize the invention(s) set out in any claims that may issue from this disclosure. Specifically and by way of example, although the headings might refer to a "Field," the claims should not be limited by the language chosen under this heading to describe the so-called field. Further, a description of a technology in the "Background" is not to be construed as an admission that certain technology is prior art to any invention(s) in this disclosure. Neither is the "Summary" to be considered as a limiting characterization of the invention(s) set forth in issued claims. Furthermore, any reference in this disclosure to "invention" in the singular should not be used to argue that there is only a single point of novelty in this disclosure. Multiple inventions may be set forth according to the limitations of the multiple claims issuing from this disclosure, and such claims accordingly define the invention(s), and their equivalents, that are protected thereby. In all instances, the scope of the claims shall be considered on their own merits in light of this disclosure, but should not be constrained by the headings set forth herein.

Use of broader terms such as "comprises", "includes", and "having" should be understood to provide support for narrower terms such as consisting of, consisting essentially of, and comprised substantially of. Use of the term "optionally," "may," "might," "possibly," and the like with respect to any element of an embodiment means that the element is not required, or alternatively, the element is required, both alternatives being within the scope of the embodiment(s). Also, references to examples are merely provided for illustrative purposes, and are not intended to be exclusive.

While several embodiments have been provided in the present disclosure, it should be understood that the disclosed systems and methods may be embodied in many other specific forms without departing from the spirit or scope of the present disclosure. The present examples are to be considered as illustrative and not restrictive, and the intention is not to be limited to the details given herein. For example, the various elements or components may be combined or integrated in another system or certain features may be omitted or not implemented. And logic flows for methods do not necessarily require the particular order shown, or sequential order, to achieve desirable results. Other steps may be provided, or steps may be eliminated, from the described flows/methods, and other components may be added to, or removed from, the described devices/systems. So, other embodiments may be within the scope of the following claims.

Also, techniques, systems, subsystems, and methods described and illustrated in the various embodiments as discrete or separate may be combined or integrated with other systems, modules, techniques, or methods without departing from the scope of the present disclosure. Other items shown or discussed as directly coupled or communicating with each other may be indirectly coupled or communicating through some interface, device, or intermediate component, whether electrically, mechanically, or otherwise. Other examples of changes, substitutions, and alterations are ascertainable by one skilled in the art and could be made without departing from the spirit and scope disclosed herein.

What is claimed is:

1. A computerized kiosk for configuring a personal protective equipment device, comprising:
    a processor;
    a non-transitory memory; and
    an application stored in the non-transitory memory that, when executed by the processor,
        reads personal information about a worker who will use a personal protective equipment device (PPE) from a database and
        configures the PPE for use by the worker based on the personal information about the worker;
        wherein the personal information about the worker comprises at least one of the following: a personal sound exposure limit for the worker, an exposure history of the worker, previous hearing damage of the worker, audiogram testing results of the worker, medical records of the worker, and medical flags of the worker.

2. The computerized kiosk of claim 1, wherein application configures the PPE via a communication coupling provided by one of a cradle or a wireless communication link.

3. The computerized kiosk of claim 1, wherein the application reads the personal information about the worker based on using one of a personal identity (PIN), an employee number, or a personal name to identify the personal information about the worker in the database.

4. The computerized kiosk of claim 1, wherein the PPE is one of a respirator, a face mask, a protective suit, or a hearing protection device.

5. The computerized kiosk of claim 1, wherein the application further:
determines an appropriate type of PPE for use by the worker based on the personal information about the worker;
determines a type of the PPE, and
configures the PPE for use by the worker only if the type of the PPE is the appropriate type of PPE for use by the worker.

6. The computerized kiosk of claim 1, wherein the application configures the PPE for use by the worker based on the personal information of the worker and the personal information of the worker further comprises at least one of the following: training records of the worker, training status of the worker, a default volume setting of the worker, a job function of the worker, a job task of the worker, an identity of a work zone authorized for the worker, training requirements for the worker, and worker job history.

7. The computerized kiosk of claim 1, further comprising a plurality of storage bins having multiple types of PPE, where the application further:
determines an appropriate type of PPE for use by the worker based on the personal information about the worker; and
dispenses the PPE of the appropriate type of PPE from the storage bins after it is configured for use by the worker based on the personal information about the worker.

8. The computerized kiosk of claim 1, where the application further uploads information from the PPE.

9. The computerized kiosk of claim 8, where the application uploads information from the PPE using a Bluetooth wireless coupling.

10. The computerized kiosk of claim 8, where the application uploads information from the PPE using a 4G wireless coupling.

11. The computerized kiosk of claim 8, where the application uploads a noise exposure measurement from the PPE.

12. The computerized kiosk of claim 8, where the application further uploads the information from the PPE to a terminal server.

13. The computerized kiosk of claim 12, where the application further downloads personal information about the worker from the terminal server.

14. The computerized kiosk of claim 1, wherein the application configures the PPE for use by the worker by actively changing the PPE.

15. The computerized kiosk of claim 14, wherein the PPE comprises a hearing protection device (hpd) and a noise exposure monitoring component; and wherein the application actively changes the PPE at least in part by setting a personal sound exposure limit for the noise exposure monitoring component using the personal information about the worker.

16. The computerized kiosk of claim 15, wherein the noise exposure monitoring component is operable to record a protected noise exposure, where the protected noise exposure is a noise exposure experienced under the hpd, and the PPE is operable to warn the worker if the protected noise exposure exceeds the pre-set personal sound exposure limit for the worker.

17. The computerized kiosk of claim 15, wherein the hpd and noise exposure monitoring component are integrated into a single PPE.

18. The computerized kiosk of claim 1, wherein the PPE further comprises a sound pass-through component and the application configures the PPE at least in part by setting a default volume level of the sound pass-through component.

19. The computerized kiosk of claim 18, wherein the sound pass-through component comprises a microphone and a speaker.

20. The computerized kiosk of claim 16, wherein setting the personal sound exposure limit comprises the kiosk storing the worker's personal sound exposure limit in the PPE, wherein the personal sound exposure limit is lower than a standard generic noise exposure limit, and wherein the PPE then uses the personal sound exposure limit as the threshold to trigger a warning regarding exposure.

* * * * *